US008659984B2

(12) United States Patent
Watanabe et al.

(10) Patent No.: US 8,659,984 B2
(45) Date of Patent: Feb. 25, 2014

(54) MEDICAL-DATA MANAGEMENT DEVICE

(71) Applicant: Panasonic Corporation, Kadoma (JP)

(72) Inventors: Katsuya Watanabe, Ehime (JP); Ikuo Honda, Chiba (JP); Kazuko Uehara, Osaka (JP); Tomonori Ohmasa, Tokyo (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/774,937

(22) Filed: Feb. 22, 2013

(65) Prior Publication Data

US 2013/0163398 A1    Jun. 27, 2013

Related U.S. Application Data

(63) Continuation of application No. PCT/JP2011/004610, filed on Aug. 18, 2011.

(30) Foreign Application Priority Data

Aug. 24, 2010   (JP) ................................. 2010-186812

(51) Int. Cl.
    *G11B 27/00* (2006.01)
(52) U.S. Cl.
    USPC .............................................. 369/83; 369/94
(58) Field of Classification Search
    USPC ................................. 369/47.15, 53.21, 83, 94
    See application file for complete search history.

(56) References Cited

U.S. PATENT DOCUMENTS

| 2005/0094516 | A1 | 5/2005 | Morimoto et al. |
| 2005/0177591 | A1 | 8/2005 | Kanda et al. |
| 2005/0251020 | A1* | 11/2005 | Kondo et al. ................. 600/407 |
| 2006/0062113 | A1* | 3/2006 | Watabe ........................ 369/47.5 |
| 2006/0072434 | A1* | 4/2006 | Shintani et al. ............ 369/272.1 |
| 2006/0153050 | A1 | 7/2006 | Mijiritskii |
| 2009/0287500 | A1* | 11/2009 | Benjamin et al. ................. 705/2 |
| 2010/0161920 | A1 | 6/2010 | Kassai |

FOREIGN PATENT DOCUMENTS

| JP | 2005-135513 | 5/2005 |
| JP | 2005-222368 | 8/2005 |
| JP | 2007-519128 | 7/2007 |
| JP | 2008-097802 | 4/2008 |
| JP | 2009-207817 | 9/2009 |
| JP | 2010-146441 | 7/2010 |

* cited by examiner

*Primary Examiner* — Brenda Bernardi
(74) *Attorney, Agent, or Firm* — Hamre, Schumann, Mueller & Larson, P.C.

(57) ABSTRACT

A medical-data management device includes: a medical data determination unit 32 that determines whether medical data to be recorded on an optical disc 14 is EMR data or not; and a medical-data access control unit 33 that causes an optical pickup 27 to access a write-once recording layer 18 of the optical disc 14 to write the data in the case where the medical data to be recorded according to a determination result of the medical data determination unit 32 is EMR data, and causes the optical pickup 27 to access rewritable recording layers 16 and 17 of the optical disc to write the data in the case where the medical data is not EMR data. A feature of the present invention is to prevent recording errors in medical data.

15 Claims, 16 Drawing Sheets

FIG. 7

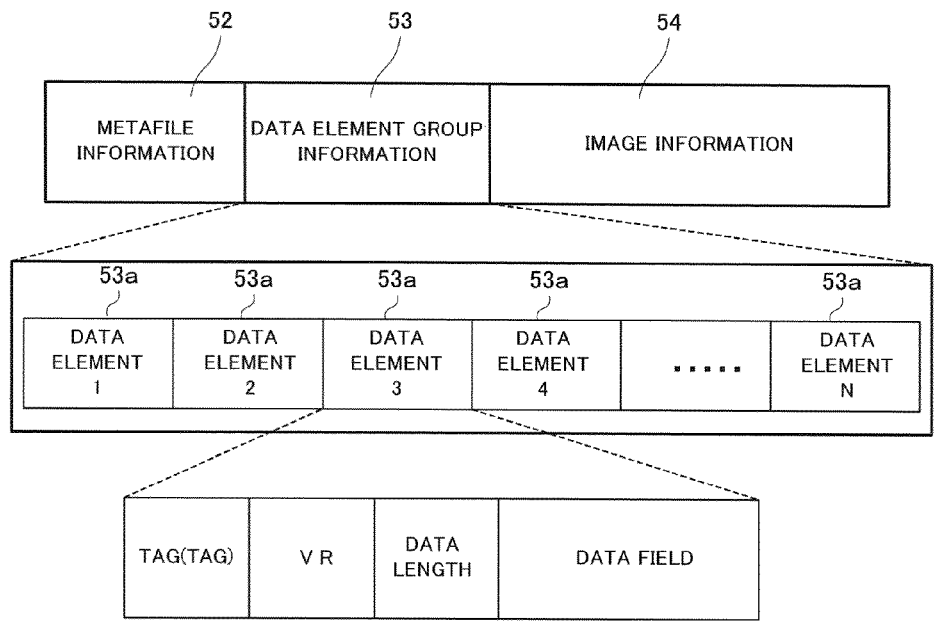

FIG. 8

| Tag | V R | Meaning |
|---|---|---|
| (0x0008, 0x0020) | DA | Test Date |
| (0x0008, 0x0030) | TM | Test Time |
| (0x0010, 0x0010) | PN | Patient's Name |
| (0x0010, 0x1010) | AS | Patient's Age |
| (0x0018, 0x0015) | CS | Tested Part |
| (0x0020, 0x0011) | IS | Series Number |
| (0x0028, 0x0004) | CS | Luminous Intensity Measurement Interpretation |
| (0x0028, 0x0010) | US | Number of Horizontally Arranged Pixels |
| (0x0028, 0x0011) | US | Number of Vertically Arranged Pixels |
| (0x0028, 0x0100) | US | Allocated Bit |
| (0x0028, 0x0101) | US | Stored Bit |
| (0x0028, 0x0102) | US | High-order Bit |
| (0x0028, 0x1050) | DS | Window Center |
| (0x0028, 0x1051) | DS | Window Width |
| (0x7fe0, 0x0010) | OW, OB | Pixel Data (Image Data) |

F I G. 9

| Binary Code | ASCII Code |
|---|---|
| 00 01 02 03 04 05 06 07 08 09 0A 0B 0C 0D 0E 0 | 0123456789ABCDEF |
| 000: 00 00 00 00 00 00 00 00 00 00 00 00 00 00 00 00 | ................ |
| 010: 00 00 00 00 00 00 00 00 00 00 00 00 00 00 00 00 | ................ |
| 020: 00 00 00 00 00 00 00 00 00 00 00 00 00 00 00 00 | ................ |
| 030: 00 00 00 00 00 00 00 00 00 00 00 00 00 00 00 00 | ................ |
| 040: 00 00 00 00 00 00 00 00 00 00 00 00 00 00 00 00 | ................ |
| 050: 00 00 00 00 00 00 00 00 00 00 00 00 00 00 00 00 | ................ |
| 060: 00 00 00 00 00 00 00 00 00 00 00 00 00 00 00 00 | ................ |
| 070: 00 00 00 00 00 00 00 00 00 00 00 00 00 00 00 00 | ................ |
| 080: 44 49 43 4d 02 00 00 00 55 4c 04 00 56 00 00 00 | DICM....UL..V... |
| 090: 02 00 01 00 4f 42 00 00 02 00 00 00 01 00 02 00 | ....OB.......... |
| 0a0: 10 00 55 49 12 00 31 2e 32 2e 38 34 30 2e 31 30 | ..UI..1.2.840.10 |
| 0b0: 30 30 38 2e 31 2e 32 00 02 00 12 00 55 49 12 00 | 008.1.2....UI.. |
| 0c0: 31 2e 32 2e 31 32 34 2e 31 31 33 35 33 32 2e 31 | 1.2.124.113532.1 |
| 0d0: 2e 31 02 00 13 00 53 48 0c 00 4d 49 54 52 41 31 | .1....SH..MITRA1 |
| 0e0: 30 53 45 50 39 36 08 00 00 00 04 00 00 00 b4 00 | 0SEP96.......... |
| 0f0: 00 00 08 00 16 00 1a 00 00 00 31 2e 32 2e 38 34 | ..........1.2.84 |

F I G. 1 0
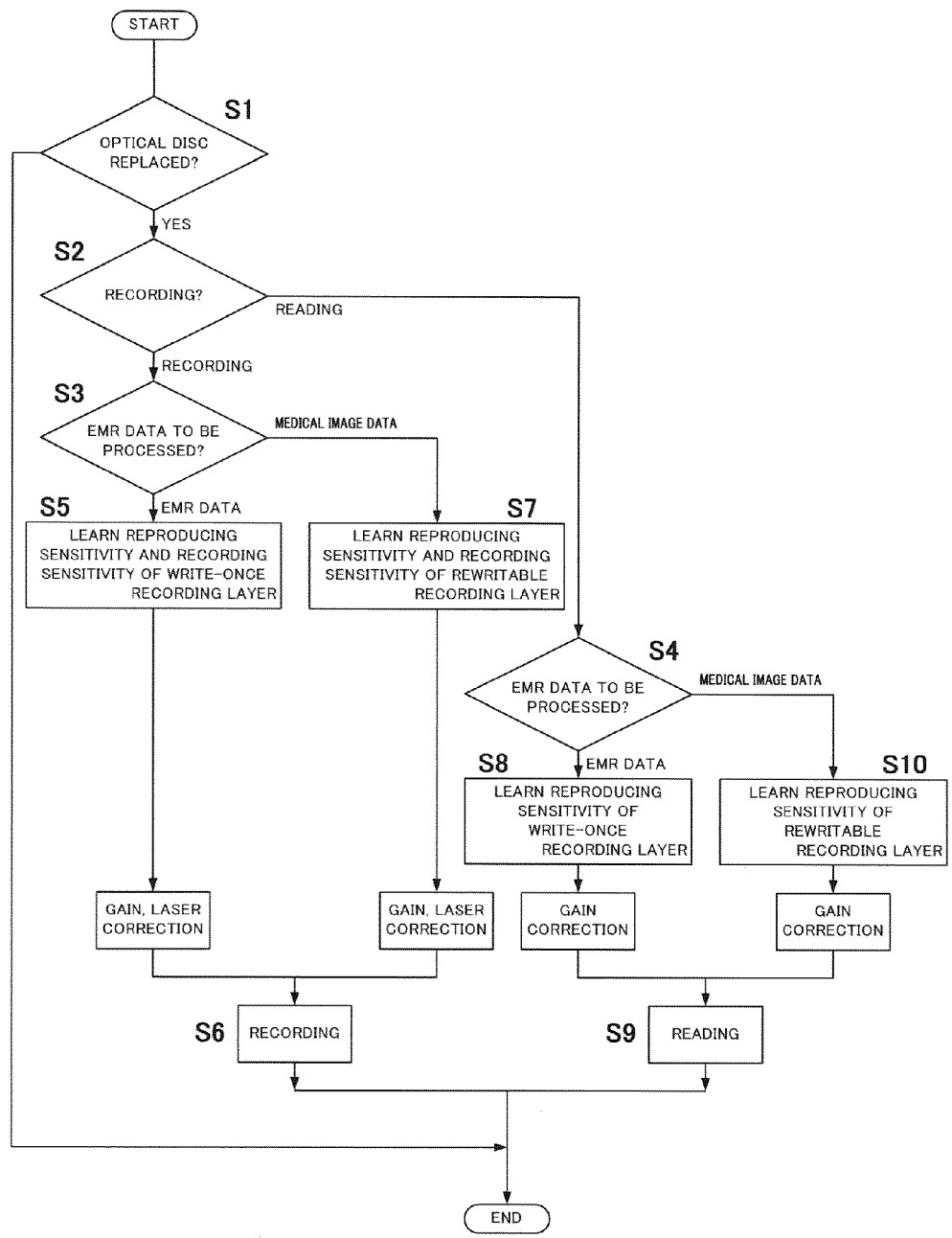

MEDICAL-DATA MANAGEMENT DEVICE

TECHNICAL FIELD

The present invention relates to a medical-data management device with an optical disc.

BACKGROUND ART

In recent years, medical images of patients have been rapidly digitized. For example, affected parts are imaged by a CR (Computed Radiography) device, a CT (Computed Tomography) device, an MRI (Magnetic Resonance Imaging) device, and so on. Image data of digitized medical images (hereinafter, will be called medical image data) is stored and managed in picture archiving and communication systems (PACS) with patient information, examination information, and so on.

Further, medical records (charts) on patient medical examinations conducted by doctors have been shifted from paper charts to electronic medical records (EMRs). EMR data of digitized medical records is prepared in client terminals installed in, for example, reception desks, clinical departments, nurses' stations, and pharmacies, and then the EMR data is stored and managed in an electronic medical record (EMR) system.

In 1999, the Ministry of Health and Welfare (then) issued a notice allowing storage of medical records in electronic media. At that time, a guideline for EMRs required three conditions: authenticity, readability, and preservability. Thus, the contents of EMR data of EMRs cannot be altered or tampered in view of authenticity.

Hence, EMR data needs to be stored in a write-once (Direct Read After Write) optical disc without being recorded as rewritable data. Medical image data is optionally updated for image processing during reuse for observing a patient's condition, education, clinical training, researches, and so on, and thus the medical image data needs to be stored in a rewritable optical disc.

In response to the need for digitization, as illustrated in FIG. 18, a hospital LAN 2 in medical practice connects medical testing apparatuses, client terminals 6 in clinical departments, nurses' stations, and so on, and a network attached storage 59 serving as a file server, enabling the following operations:

In this case, personal information including a patient's name in a diagnosis has been written as EMR data in an electronic medical record (EMR) system 60. Medical image data of a test conducted on a patient by a medical testing apparatus 4 in a diagnosis has been written in an image server 61 in relation to the EMR data.

First, a doctor (hereinafter, including a radiologist) observes medical image data displayed on the image viewer screen of the client terminal 6 (image diagnosis and interpretation).

The doctor then performs image processing, e.g., gradation processing or addition of annotation data on the medical image data displayed on the image viewer screen.

The doctor then pastes the image-processed medical image data displayed on the image viewer screen onto the screen of an EMR by dragging and dropping. Specifically, the image-processed medical image data is converted to general-purpose image data (e.g., JPEG) having low resolution and a small volume, and then the data is pasted onto the screen of the EMR.

The doctor then examines a patient while referring to the medical image data displayed on the image viewer screen, and creates medical record data on the screen of the EMR. The doctor then stores the medical record data in the electronic medical record (EMR) system 60 along with the pasted general-purpose image data on the screen of the EMR.

Moreover, according to the progress of a patient's condition, the doctor refers to past medical record data stored in the electronic medical record (EMR) system 60 and general-purpose image data corresponding to the medical record data in the image server 61 of a picture archiving and communication system. Medical image data corresponding to the past general-purpose image data displayed on the screen of the EMR is displayed on the image viewer screen, and then the data may be stored again after being subjected to different image processing from that of the past reference (For example, see Patent Literature 1).

In preparation for failures such as damages on the image server 61 and the electronic medical record (EMR) system 60, medical image data is duplicated and stored on a rewritable optical disc set in an optical disc drive 62 of the image server 61. Furthermore, EMR data is duplicated and stored on a write-once optical disc set in an optical disc drive 63 of the electronic medical record (EMR) system 60.

Patent Literature 2 describes a hybrid optical disc including a rewritable recording layer and a write-once recording layer.

CITATION LIST

Patent Literature

Patent Literature 1: Japanese Patent Laid-Open No. 2009-207817
Patent Literature 2: National Publication of International Patent Application No. 2007-519128

SUMMARY OF INVENTION

Technical Problem

The conventional medical-data management device duplicates and stores data separately on two optical discs: the rewritable optical disc of the image server 61 and the write-once optical disc of the electronic medical record (EMR) system 60. Thus, operations need to be performed with the two optical discs, resulting in low usability.

The hybrid optical disc described in Patent Literature 2 can achieve higher usability than in the case where the rewritable optical disc and the write-once optical disc are prepared to store EMRs and medical image data on the respective optical discs.

However, each time a user stores an EMR and medical image data, the user selects a storage destination. Thus, an erroneous selecting operation may cause erroneous writing of EMR data in the rewritable recording layer of the hybrid optical disc or erroneous writing of medical image data in the write-once recording layer of the hybrid optical disc, as in the case of separate duplication storage on the two optical discs.

An object of the present invention is to provide a medical-data management device that can prevent the occurrence of human errors, improve usability by means of a hybrid optical disc, and eliminate errors when EMR data and medical image data are stored in recording layers.

Solution to Problem

A medical-data management device according to the present invention is a medical-data management device that records medical data on an optical disc including a rewritable recording layer and a write-once recording layer, the medical-data management device including: a medical data determination unit that determines whether the medical data to be recorded on the optical disc is EMR data or not; and a medical-data access control unit that causes an optical pickup to access the write-once recording layer of the optical disc to write the data in the case where the medical data to be recorded according to the determination result of the medical data determination unit is EMR data, and causes the optical pickup to access the rewritable recording layer of the optical disc to write the medical data in the case where the medical data is not EMR data.

A medical-data management device according to the present invention is a medical-data management device that reads medical data from an optical disc including a rewritable recording layer and a write-once recording layer, the medical-data management device including: a medical data determination unit that determines whether the medical data to be read from the optical disc is EMR data or not; and a medical-data access control unit that causes an optical pickup to access the write-once recording layer of the optical disc to read the data in the case where the medical data to be read according to the determination result of the medical data determination unit is EMR data, and causes the optical pickup to access the rewritable recording layer of the optical disc to read the data in the case where the medical data is not EMR data.

Advantageous Effects of Invention

With this configuration, the medical data determination unit automatically determines the contents of medical data and instructs the medical-data access control unit to write the medical data on the optical disc, thereby preventing the occurrence of human errors. EMR data can be correctly stored in the write-once recording layer while medical image data can be correctly stored in the write-once recording layer.

BRIEF DESCRIPTION OF DRAWINGS

FIG. 7 is a structural diagram of medical image data according to the DICOM standard.

FIG. 8 shows the relationship between TAG and VR of medical image data according to the DICOM standard.

FIG. 9 is an explanatory drawing showing medical image data according to the DICOM standard.

FIG. 10 is a flowchart showing the operations of a layer learning unit in the data management device according to the first embodiment of the present invention.

DESCRIPTION OF EMBODIMENTS

Referring to FIGS. 1 to 17, embodiments of a medical-data management device according to the present invention will be described below.

First Embodiment

FIGS. 1 to 11 illustrate a first embodiment of the present invention.

Figure 1:
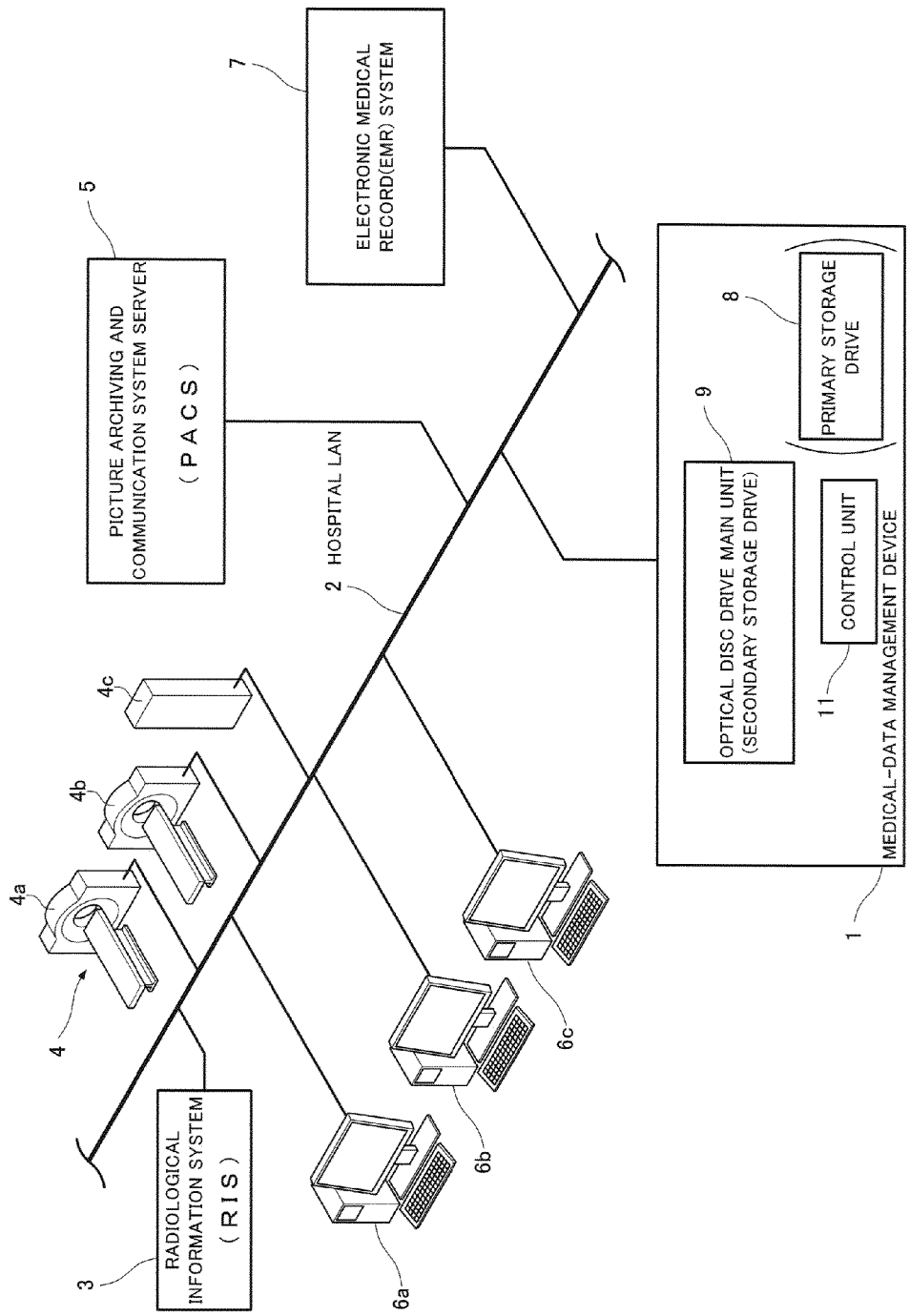
FIG. 1 is a system diagram of a hospital using a data management device according to a first embodiment of the present invention.

FIG. 1 shows a connected state of a hospital LAN 2 using a medical-data management device 1 according to the present invention.

The hospital LAN 2, which is a communication network, connects a radiological information system (RIS) 3, a medical testing apparatus 4 including a CR (Computed Radiography) apparatus, a CT (Computed Tomography) apparatus, and an MRI (Magnetic Resonance Imaging) apparatus that act as modalities, a picture archiving and communication system (PACS) server 5, a plurality of client terminals 6a to 6c installed in clinical departments such as a radiology department, a nurse station, and a pharmacy, an electronic medical record (EMR) system 7, and the medical-data management device 1 in a state in which data communications can be carried out.

The radiological information system 3 manages information on examination reservations, reports on diagnosis results, achievement control, and stock control in the department of radiology. The radiological information system 3 transmits imaging order information from the electronic medical record (EMR) system 7 to the medical testing apparatus 4 and the picture archiving and communication system server 5.

Specifically, the medical testing apparatus 4 includes MRI apparatuses 4a and 4b and an X-ray apparatus 4c. The medical testing apparatus 4 generates images of a patient according to the imaging order information received from the radiological information system 3, and creates medical image data. Moreover, the medical testing apparatus 4 creates image associated information for the medical image data according to the imaging order information. Furthermore, the medical testing apparatus 4 associates the image associated information with the medical image data to create DICOM image data in compliance with the DICOM (Digital Imaging and Communication in Medicine) standard and transmits the data to the picture archiving and communication system server 5.

The medical testing apparatus 4 may be a CR apparatus, a CT apparatus, or an MRI apparatus. Imaging apparatuses for various kinds of medical images are also applicable. The image associated information includes patient information, examination information, series information, and image information. The patient information concerns patients. The examination information concerns examinations. The series information concerns a unit of a series of medical image data created in each imaging apparatus during an examination. The image information concerns medical image data.

The picture archiving and communication system server 5 is an image server that stores and manages DICOM image data. The picture archiving and communication system server 5 transmits DICOM image data, image processing information, and so on in response to a data acquisition request received from another apparatus. The picture archiving and communication system server 5 also stores and manages image processing information for DICOM image data created in the client terminals 6a to 6c.

Specifically, the image processing information includes annotation data, gradation processing information, and scaling information about medical image data. The scaling information is information to be referred to during scaling of images to a legible size for a user. The image processing information includes image information. The DICOM image data and the image processing information are managed while being associated with each other by the image information.

The electronic medical record (EMR) system 7 has a medical record data managing function of storing and managing medical record data, and stores the conditions and diagnostic results of patients. The electronic medical record (EMR) system 7 stores medical record data created in the client terminals 6a to 6c and general-purpose JPEG image data that is associated with the medical record data displayed on the client terminals 6a to 6c. The medical record data includes patient information, examination information, series information, and image information. The general-purpose image data is associated with the image information. The medical record data and the general-purpose image data are associated with each other by the image information. The electronic medical record (EMR) system 7 generates imaging order information for requesting imaging of a patient based on instruction signals from the client terminals 6a to 6c and so on, and transmits the information to the radiological information system 3.

The client terminals 6a to 6c have an image viewer function of displaying DICOM image data and a medical record data creating function of creating medical record data. The image viewer function of the client terminals 6a to 6c is used for a reading operation by a doctor and an imaging operation by a radiographer.

Specifically, the client terminals 6a to 6c acquire DICOM image data from the picture archiving and communication system server 5 and display medical image data or the like based on the DICOM image data. Furthermore, the client terminals 6a to 6c transmit created image processing information in response to a user operation to the picture archiving and communication system server 5. The image processing information includes annotation data, gradation processing information, and/or scaling information about the medical image data.

The medical record data creating function of the client terminals 6a to 6c is used for a diagnosis of a patient by a doctor in each clinical department.

Specifically, the client terminals 6a to 6c acquire EMR associated data such as medical record data and general-purpose image data from the electronic medical record (EMR) system 7. The client terminals 6a to 6c then display the medical record data and the general-purpose image data based on the acquired EMR associated data, creates (or updates) medical record data and so on in response to a user operation, and transmits the created EMR data to the electronic medical record (EMR) system 7. In the case where additional general-purpose image data is displayed, the general-purpose image data is also transmitted to the electronic medical record (EMR) system 7.

The medical-data management device 1 has a storage function of providing file sharing service. For example, the medical-data management device 1 includes a primary storage drive 8 composed of a hard disk or an SSD (Solid State Drive), an optical disc drive main unit 9 serving as a secondary storage drive, and a control unit 11 that manages and controls the primary storage drive 8 and the optical disc drive main unit 9. In the case of primary storage on the server, the primary storage drive 8 is not necessary in the medical-data management device 1.

In the case where the medical-data management device 1 includes the primary storage drive 8 and the optical disc drive main unit 9, a virtual optical disc is first created on the primary storage drive 8 and then is simply copied to an actual optical disc loaded in the optical disc drive main unit 9. In this case, primary storage is performed on the server without the provision of the primary storage drive 8 in the medical-data management device 1. A specific configuration of the medical-data management device 1 of this example will be described below.

The apparatuses connected to the hospital LAN 2 can store various files by means of the optical disc drive main unit 9 of the medical-data management device 1. The apparatuses can acquire the stored files from the optical disc drive main unit 9 of the medical-data management device 1.

Figure 2A:
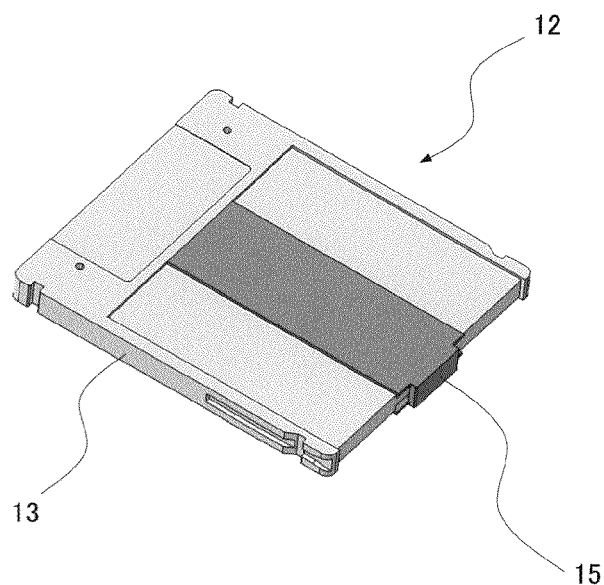
FIG. 2(a) is a perspective view illustrating an optical disc with a cartridge used for the data management device.
Figure 2B:
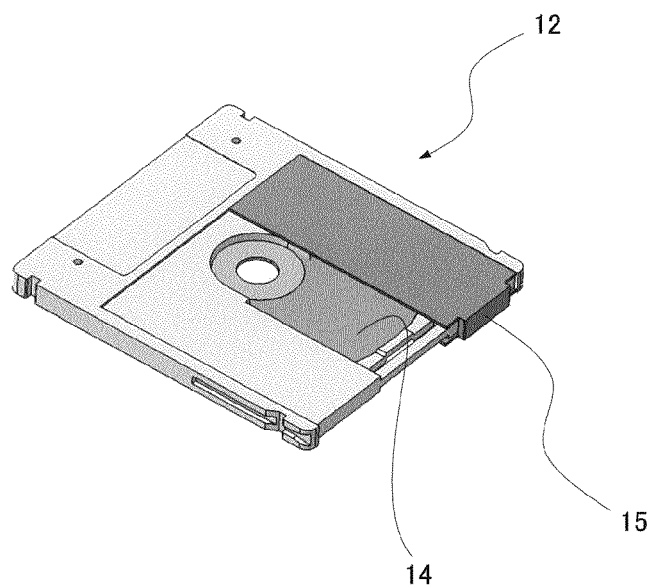
FIG. 2(b) is a perspective view illustrating the optical disc with an opened shutter.

EMRs stored in the electronic medical record (EMR) system 7 and medical image data stored in the picture archiving and communication system server 5 can be duplicated and stored on an optical disc 12 with a cartridge in FIG. 2 from the client terminal 6a. The optical disc 12 with the cartridge is set and used in the optical disc drive main unit 9 and includes an optical disc 14 that is rotatably stored in a cartridge 13. In the case where information is written or read on the optical disc 14, a shutter 15 slides to open as illustrated in FIG. 2(b), allowing writing and reading of information on the exposed optical disc 14.

Figure 3:
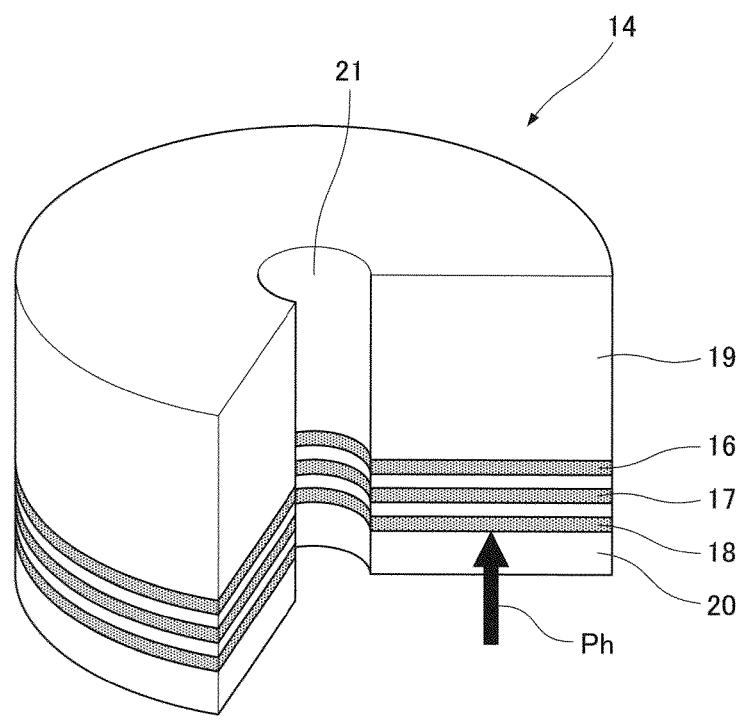
FIG. 3 is a partially cutaway perspective view schematically illustrating the optical disc.

As illustrated in FIG. 3, the disc-like optical disc 14 is a multilayer hybrid optical disc including rewritable recording layers 16 and 17 and a non-writable write-once recording layer 18.

Figure 4:
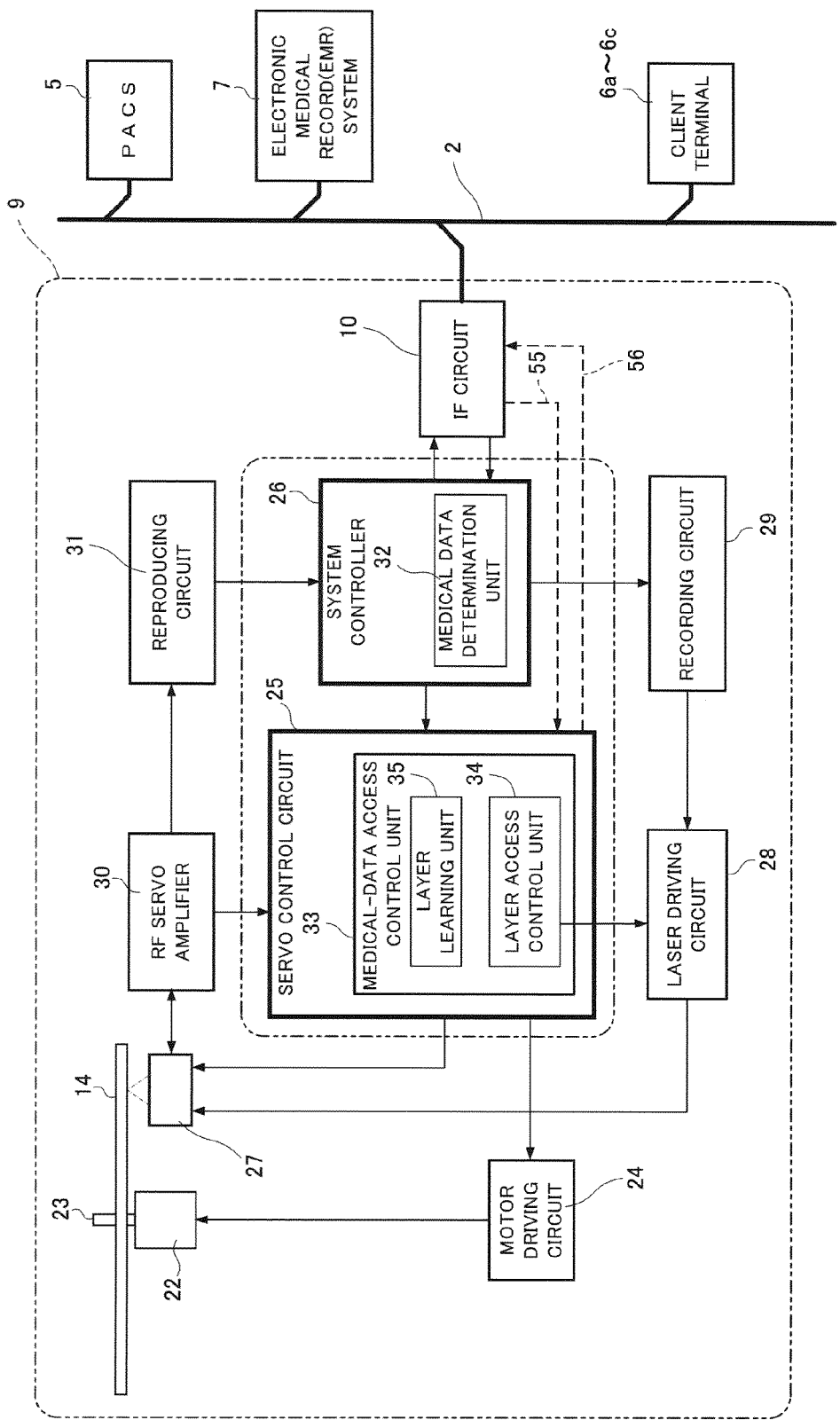
FIG. 4 is a structural diagram of the medical-data management device with the optical disc.

Specifically, the optical disc 14 includes a thick substrate 19 at the top and a thin cover layer 20 at the bottom. In this state, the write-once recording layer 18 is provided on the inner bottom surface, and the rewritable recording layers 16 and 17 are disposed above the write-once recording layer 18. Reference numeral 21 denotes a vertical through hole. A rotating shaft 23 of a disc motor 22 in the optical disc drive main unit 9 in FIG. 4 is inserted into the through hole 21. Ph represents a laser beam for writing/reading access to the optical disc 14 and the direction of incidence of the laser beam.

FIG. 4 is a structural diagram illustrating the medical-data management device using the optical disc according to the present embodiment.

The optical disc drive main unit 9 in FIG. 4 will be described below.

The disc motor 22 in the optical disc drive main unit 9 is rotated by a motor driving circuit 24. The motor driving circuit 24 is connected to a servo control circuit 25. The servo control circuit 25 is connected to a system controller 26. The system controller 26 is connected to the client terminals 6a to 6c, the electronic medical record (EMR) system 7, the picture archiving and communication system server 5, and so on via an IF circuit 10 and the hospital LAN 2.

Thus, the client terminals 6a to 6c can duplicate and store EMR data and medical image data on the optical disc 14 and read the duplicated and stored EMRs and medical image data by means of the medical-data management device 1. The EMR data is duplicated and stored in the write-once recording layer 18 of the optical disc 14. The medical image data is duplicated and stored in the rewritable recording layers 16 and 17 of the optical disc 14 and thus can be optionally rewritten and updated later.

Data is written and read on the optical disc 14 by an optical pickup 27 provided under the optical disc 14. The optical pickup 27 is connected to the system controller 26 via a laser driving circuit 28 and a recording circuit 29.

The servo control circuit 25 moves the optical pickup 27 inward or outward in the radial direction of the optical disc 14 and in such a direction that the optical pickup 27 comes close to or separates from the optical disc 14. Data read from the optical disc 14 through the optical pickup 27 is transmitted to the system controller 26 through an RF servo amplifier 30 and a reproducing circuit 31.

The system controller 26 contains a system program that allows a typical optical disc drive to access the optical disc 14 to read or write data, and a program necessary for allowing a microcomputer to operate a medical data determination unit 32 that determines whether medical data received through the IF circuit 10 and the hospital LAN 2 is EMR data or not.

The servo control circuit 25 contains a system program that allows a typical optical disc drive to access the optical disc 14 to read or write data and a medical-data access control unit 33. The medical-data access control unit 33 includes a layer access control unit 34 that drives the optical pickup 27 so as to access proper one of the rewritable recording layers 16 and 17 and the write-once recording layer 18 of the optical disc 14 according to the determination result of the medical data determination unit 32, and a layer learning unit 35 that learns the recording sensitivity/reproducing sensitivity of the set optical disc 14 when medical data is recorded on or reproduced from the optical disc 14.

Figure 5:
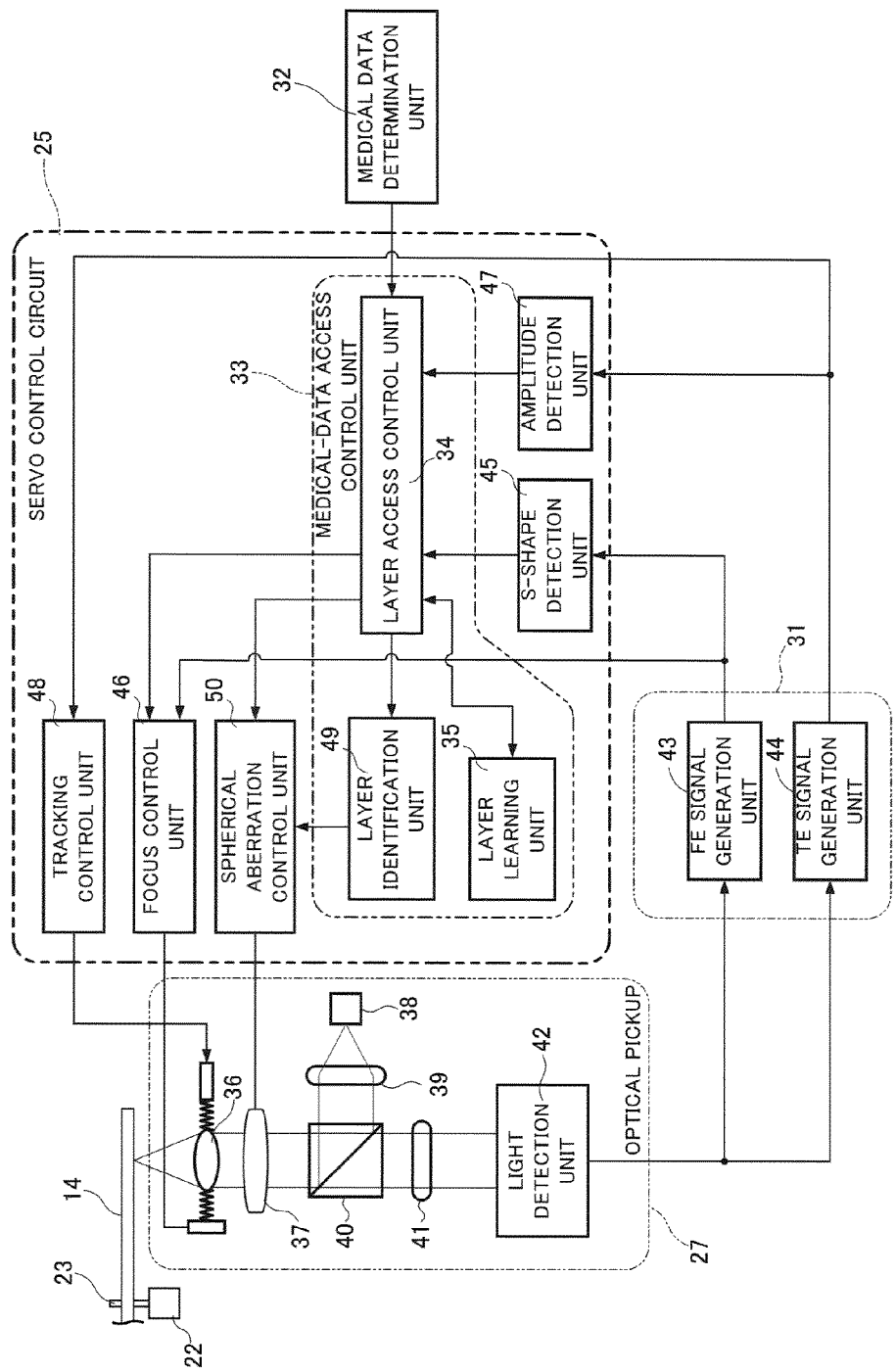
FIG. 5 is a structural diagram of a servo control circuit and an optical pickup in FIG. 4 and the periphery.

FIG. 5 is a structural diagram specifically illustrating the configuration of the principal part of FIG. 4. Referring to FIGS. 5 and 6 to 11, the configurations of the medical data determination unit 32, the layer access control unit 34, and the layer learning unit 35 will be specifically described below.

The layer access control unit 34 receives the address of an image to be accessed from the system controller. After that, the layer access control unit 34 moves the optical pickup 27 to one of the layers of the optical disc 14 according to the address of the image, thereby making access to the data of the layer.

The optical pickup 27 includes an objective lens 36 opposed to the undersurface of the optical disc 14 and an aberration correction lens 37 disposed below the objective lens 36. The laser beam Ph from a light source 38 reaches the optical disc 14 through a collimating lens 39, a mirror 40, the aberration correction lens 37, and the objective lens 36.

Light reflected from the optical disc 14 reaches a light detection unit 42 through the objective lens 36, the aberration correction lens 37, the mirror 40, and a collimating lens 41. In response to a light signal having reached the light detection unit 42, a focus error signal is generated in an FE signal generation unit 43, and a tracking error signal is generated in a TE signal generation unit 44.

The focus error signal generated in the FE signal generation unit 43 is supplied to an S-shape detection unit 45 and a focus control unit 46, enabling focus control on the objective lens 36.

The tracking error signal generated in the TE signal generation unit 44 is supplied to an amplitude detection unit 47 and a tracking control unit 48, enabling tracking control on the objective lens 36.

The outputs of the S-shape detection unit 45 and the amplitude detection unit 47 are supplied to the layer access control unit 34. The layer access control unit 34 controls the output power of the light source 38 based on the learning result of the layer learning unit 35. The layer access control unit 34 drives the aberration correction lens 37 through a layer identification unit 49 and a spherical aberration control unit 50 in such a direction that the aberration correction lens 37 comes close to or separates from the optical disc 14 depending on the recording layer to be accessed, based on the determination result of the medical data determination unit 32.

An output from the layer access control unit 34 is supplied to the focus control unit 46. The output from the layer access control unit 34 is also supplied to the spherical aberration control unit 50 and the layer identification unit 49, allowing the spherical aberration control unit 50 to correct a spherical aberration through the aberration correction lens 37.

Figure 6A:
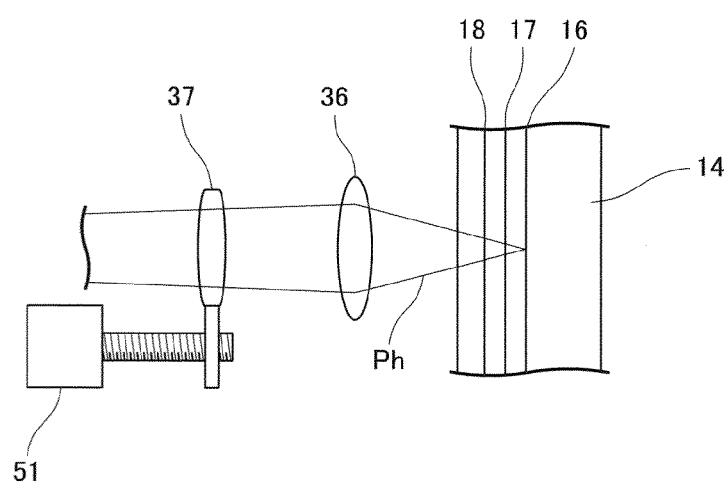
FIG. 6(a) is an explanatory drawing illustrating the optical pickup that accesses a rewritable recording layer in the optical disc to read and write medical image data.

In a state in which the optical disc 14 is set on the rotating shaft 23, medical image data is read or written by accessing the rewritable recording layer 16 of the optical disc 14 as illustrated in FIG. 6(a).

First, the objective lens 36 is moved to the optical disc 14, the aberration correction lens 37 is moved in this state to the optical disc 14 by a driving device 51, and the laser beam Ph is focused onto the rewritable recording layer 16 to read or write the medical image data.

In the case where medical image data is read or written in the rewritable recording layer 17, the aberration correction lens 37 is first moved opposite to the optical disc 14 by the driving device 51, the objective lens 36 is moved opposite to the optical disc 14, and the laser beam is focused onto the rewritable recording layer 17 to read or write the medical image data.

Figure 6B:
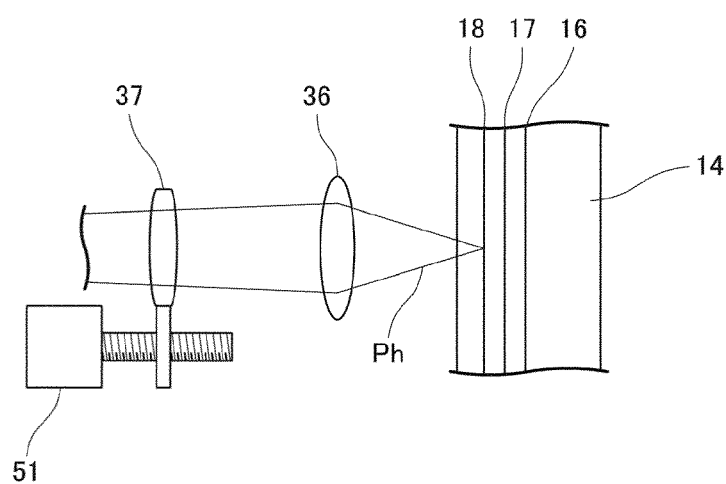
FIG. 6(b) is an explanatory drawing illustrating the optical pickup that accesses a write-once recording layer in the optical disc to read and write EMR data.

In the case where EMR data is read or written in the write-once recording layer 18, as illustrated in FIG. 6(b), the aberration correction lens 37 and the objective lens 36 are moved opposite to the optical disc 14 to focus the light beam onto the write-once recording layer 18, enabling reading and writing of the EMR data.

The configuration of the medical data determination unit 32 will be specifically described below. The medical data determination unit 32 determines whether medical data received from the hospital LAN 2 through the IF circuit 10 is EMR data or not.

Regarding the EMR data and medical image data of medical data, public standards or industry standards are not provided for the data format of EMR data under the present circumstances. Thus, the format of recorded and stored EMR data varies depending upon company systems. In consideration of the characteristics of medical records, freely written sentences or handwritten drawings need to be frequently used to express patient's conditions. Thus, it is difficult to express data as a structure.

The data format of medical image data is defined by the DICOM standard. Hence, whether medical data is EMR data or medical image data can be exclusively determined depending upon whether or not the data is defined by the DICOM standard, which is a typical standard of medical image data. Specifically, data can be identified by examining the contents of a buffer (not shown) in the system controller 26. The contents will be specifically described below.

FIG. 7 shows the data structure of a DICOM image data file. As shown in FIG. 7, the overall file of DICOM image data is composed of three pieces of information: metafile information 52, data element group information 53, and image information 54.

As shown in FIG. 7, the data element group information 53 is composed of multiple data elements 53*a* (in FIG. 7, data elements 1, 2, 3, 4, . . . N). The data elements 53*a* are each provided with a tag (TAG), VR (Value R-epresentations), and a data length given to an actual data field. FIG. 8 shows a table of TAGs, VRs, and the meanings thereof. Specifically, received medical data can be identified as medical image data when it is detected that at least one of the tag (TAG) and VR of the received medical data complies with the DICOM standard.

For example, it is detected whether or not one of the data elements 53*a* of received medical data has a tag of "0010, 0010" or VR of "PN". In the case where "0010, 0010" or "PN" can be detected, the received medical data can be identified as DICOM image data, not EMR data.

The reliability of determination can be improved by detecting whether or not one of the data elements 53*a* of received medical data has a tag of "0010, 0010" and VR of "PN" next to the tag. In addition to a combination of determination conditions of the tag and the VR, a combination of tags or a combination of VRs according to the DICOM standard may be used.

In the specific example, whether medical data is EMR data or not is determined by one or both of the tag (TAG) and VR of the medical data. The determination can be made sooner.

FIG. 9 shows an example of a DUMP list of DICOM data on actual medical images.

As shown in FIG. 9, the DICOM data contains 0x00 of 128 bytes at the beginning. A flag "DICM" from 129 byte to 132 byte is expressed as a character string to indicate a declaration that the data is DICOM data. The pattern detection of the character string makes it possible to quickly identify the data as DICOM medical image data at the beginning of the data.

The reliability of determination on whether received medical data is EMR data or not can be further improved by combining the tag and VR of the same medical data and the presence or absence of the character string of the flag "DICM", though the time for determination cannot be shortened.

In the case where the data format of EMRs is standardized in the future, whether received medical data is EMR data or not may be determined depending upon the data structure, the first declaration, the character string of the definition, and so on as in the case of a medical image of the DICOM standard.

It can be determined whether medical data received by the medical data determination unit 32 is EMR data or medical image data, according to the contents of the medical data. Thus, in the case where the medical data determination unit 32 determines that medical data is EMR data, the medical-data access control unit 33 causes the optical pickup 27 to access the write-once recording layer 18 of the optical disc 14 to read or write the medical data. In the case where the medical data determination unit 32 determines that medical data is medical image data, the medical-data access control unit 33 causes the optical pickup 27 to access the rewritable recording layer 16 or the rewritable recording layer 17 of the optical disc 14 to read or write the medical data.

The medical data determination unit 32 automatically determines whether medical data to be processed is EMR data or medical image data, and controls the servo control circuit 25. Particularly, when medical data is written on the optical disc 14, it is not necessary to specify the recording layer of the optical disc 14 from the client terminals 6*a* to 6*c*. EMR data received by the medical-data management device 1 is correctly written into the write-once recording layer 18, and medical image data received by the medical-data management device 1 is correctly written in the rewritable recording layer 16 or the rewritable recording layer 17.

In the case where the medical data determination unit 32 is not provided, when a command for writing EMR data on the optical disc 14 is inputted from the client terminals 6*a* to 6*c*, a writing command to the rewritable recording layers 16 and 17 may be erroneously issued due to an operational error. In this case, EMR data is recorded. In other words, in the case where the rewritable recording layer 16 or 17 is erroneously specified as a recording layer where data is to be written, EMRs are disturbed. In the first embodiment, the provision of the medical data determination unit 32 can improve operability and the reliability of EMRs.

FIG. 10 is a flowchart showing control operations of the layer learning unit 35.

In step S1, it is detected that the optical disc 12 with the cartridge has been loaded or unloaded in the optical disc drive main unit 9. In step S2, it is determined whether a command issued later through the IF circuit 10 and the hospital LAN 2 is a recording command or a reading command. In the case where it is determined in step S2 that the command is a recording command, step S3 is performed. In the case where it is determined in step S2 that the command is a reading command, step S4 is performed.

In step S3, it is determined whether the determination result of the medical data determination unit 32 is EMR data or medical image data. In the case of EMR data, in step S5, the optical pickup 27 accesses the write-once recording layer 18 of the replaced optical disc 14 to learn the state of the recording layer. Specifically, the reproducing sensitivity of the write-once recording layer 18 is measured, the write-once recording layer 18 undergoes test recording, and then data is reproduced at a test recording point to learn recording sensitivity.

In step S6 following step S5, EMR data determined in step S3 from medical data to be processed is recorded in the write-once recording layer 18 after the gains of the tracking control unit 48 and the focus control unit 46 are corrected through the layer access control unit 34 based on a learning result in step S5.

In the case where it is determined in step S3 that medical image data is to be processed, the optical pickup 27 accesses one of the rewritable recording layer 16 and the rewritable recording layer 17 of the replaced optical disc 14 in step S7 to learn the state of the recording layer. Specifically, the reproducing sensitivity of the rewritable recording layer 16 or the rewritable recording layer 17 is measured, the rewritable recording layer 16 or the rewritable recording layer 17 undergoes test recording, and then data is reproduced at a test recording point to learn recording sensitivity.

In step S6 following step S7, medical image data determined in step S3 from medical data to be processed is recorded in the rewritable recording layer where data is to be recorded, after the gain of the tracking control unit 48, the gain of the focus control unit 46, and the laser output value of the laser driving circuit 28 are corrected through the layer access control unit 34 based on a learning result in step S7.

In the case where it is determined in step S2 that a command is a reading command, it is determined in step S4 whether a determination result in the medical data determination unit 32 is EMR data or medical image data. In the case of EMR data, in step S8, the write-once recording layer 18 of the replaced optical disc 14 is irradiated with the laser beam Ph by the optical pickup 27 to learn the reproducing sensitivity of the write-once recording layer 18.

In step S9 following the S8, the gain of the tracking control unit 48, the gain of the focus control unit 46, and the gain of the reproducing circuit 31 are corrected through the layer access control unit 34 based on a learning result in step S8, and the optical pickup 27 accesses the write-once recording layer 18 to read EMR data determined in step S4 from medical data to be processed.

In the case where it is determined in step S4 that medical image data is to be processed, in step S10, the rewritable recording layers 16 and 17 of the replaced optical disc 14 are sequentially irradiated with the laser beam Ph by the optical pickup 27 to learn the reproducing sensitivity of the rewritable recording layers 16 and 17.

In step S9 following step S10, the gain of the tracking control unit 48, the gain of the focus control unit 46, and the gain of the reproducing circuit 31 are corrected through the layer access control unit 34 based on a learning result in step S10, and the optical pickup 27 sequentially accesses the rewritable recording layers 16 and 17 to read medical image data determined in step S4 from medical data to be processed.

In the case of recording immediately after the replacement of the optical disc 11 with the cartridge, one of step S5 and step S7 is performed to learn only the recording sensitivity of the write-once recording layer 18 or the rewritable recording layers 16 and 17, and then in step S6, medical data is quickly recorded on the optical disc 14. Thus, a starting time can be shorter immediately after the replacement of the optical disc 12 with the cartridge, as compared with recording on all of the rewritable recording layers 16 and 17 and the write-once recording layer 18 after the reproducing sensitivity and recording sensitivity of the recording layers are learned.

In the case of reading immediately after the replacement of the optical disc 12 with the cartridge, one of step S8 and step S10 is performed to learn only the reproducing sensitivity of the write-once recording layer 18 or the rewritable recording layers 16 and 17, and then in step S9, medical data is quickly read from the optical disc 14. Thus, a starting time can be shorter immediately after the replacement of the optical disc 12 with the cartridge, as compared with reading on all of the rewritable recording layers 16 and 17 and the write-once recording layer 18 after the recording sensitivity and reproducing sensitivity of the recording layers are learned.

As illustrated in FIG. 3, the write-once recording layer 18 of the optical disc 14 is located between the rewritable recording layers 16 and 17 and the objective lens 36.

In other words, the output power of the laser beam Ph at the inner recording layer decreases because data is written in the inner recording layer through the outer recording layer. Conversely, the output power of the laser beam Ph increases in the outer recording layer.

Figure 11A:
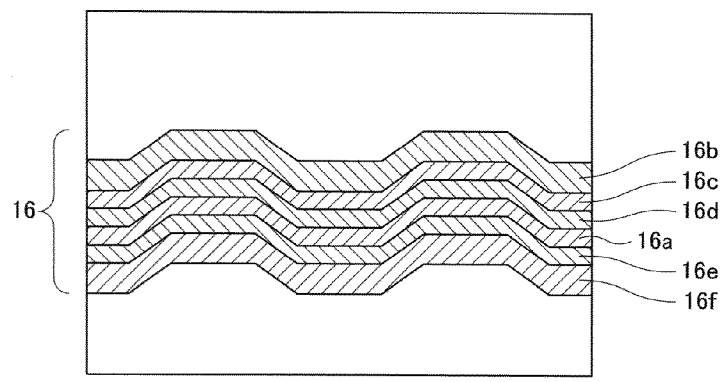
FIG. 11(a) is a cross-sectional view illustrating the composition of a rewritable recording layer 16 of the optical disc.
Figure 11B:
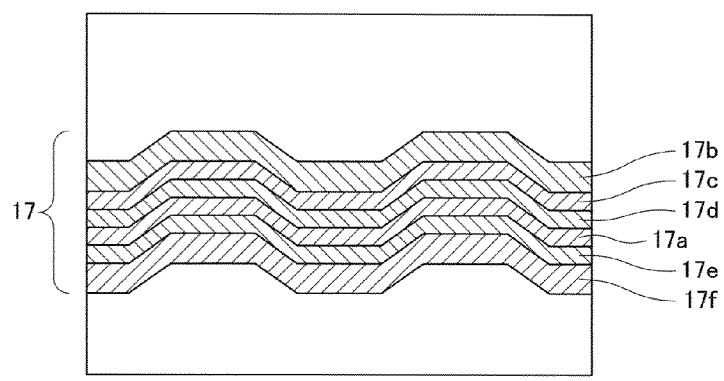
FIG. 11(b) is a cross-sectional view illustrating the composition of a rewritable recording layer 17 of the optical disc.
Figure 11C:
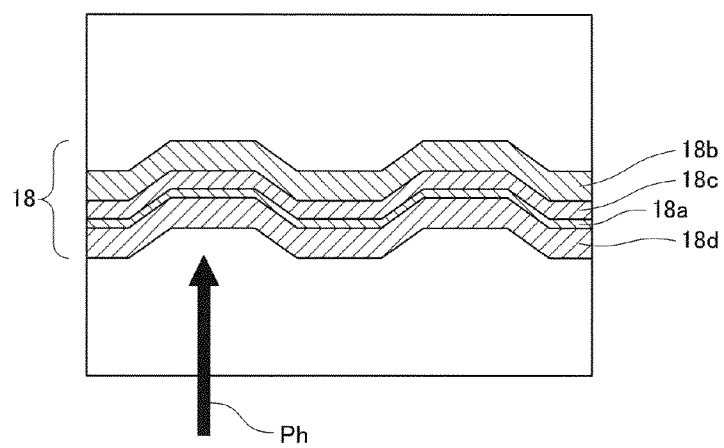
FIG. 11(c) is a cross-sectional view illustrating the composition of a write-once recording layer 18 of the optical disc.

FIG. 11(a) is a cross-sectional view of the rewritable recording layer 16. FIG. 11(b) is a cross-sectional view of the rewritable recording layer 17. FIG. 11(c) is a cross-sectional view of the write-once recording layer 18.

In FIG. 11(a), the rewritable recording layer 16 includes a recording film 16a, a reflective layer 16b, a protective layer 16c, an interface layer 16d, an interface layer 16e, and a protective layer 16f. In FIG. 11(b), the rewritable recording layer 17 includes a recording film 17a, a transmittance adjusting layer 17b, a reflective layer 17c, an interface layer 17d, an interface layer 17e, and a protective layer 17f. In FIG. 11(c), the write-once recording layer 18 includes a recording film 18a, a reflective layer 18b, a protective layer 18c, and a protective layer 18d.

As illustrated in FIGS. 11(a), 11(b), and 11(c), the write-once recording layer 18 can have fewer layers (films) than the rewritable recording layers 16 and 17. Thus, a transmittance is easily raised in the write-once recording layer 18. The write-once recording layer 18 is advantageously located outside the rewritable recording layers 16 and 17.

In the case where the rewritable recording layers 16 and 17 are located outside the write-once recording layer 18, a large output power of the laser beam Ph is applied to the recording films 16a and 17b of the rewritable recording layers 16 and 17 during writing on the write-once recording layer 18. Rewriting repeated at the same location is likely to deteriorate the recording films 16a and 17b of the rewritable recording layers 16 and 17. Thus, in consideration of the reliability of recording/storage of medical image data written in the rewritable recording layers 16 and 17, the write-once recording layer 18 is advantageously located outside the rewritable recording layers 16 and 17.

The write-once recording layer 18 contains beforehand a system boot program necessary for recovery and an image viewer program for viewing the data of the picture archiving and communication system 5 as well as tamper-proof EMR data, achieving a more convenient recording medium.

Second Embodiment

Figure 12:
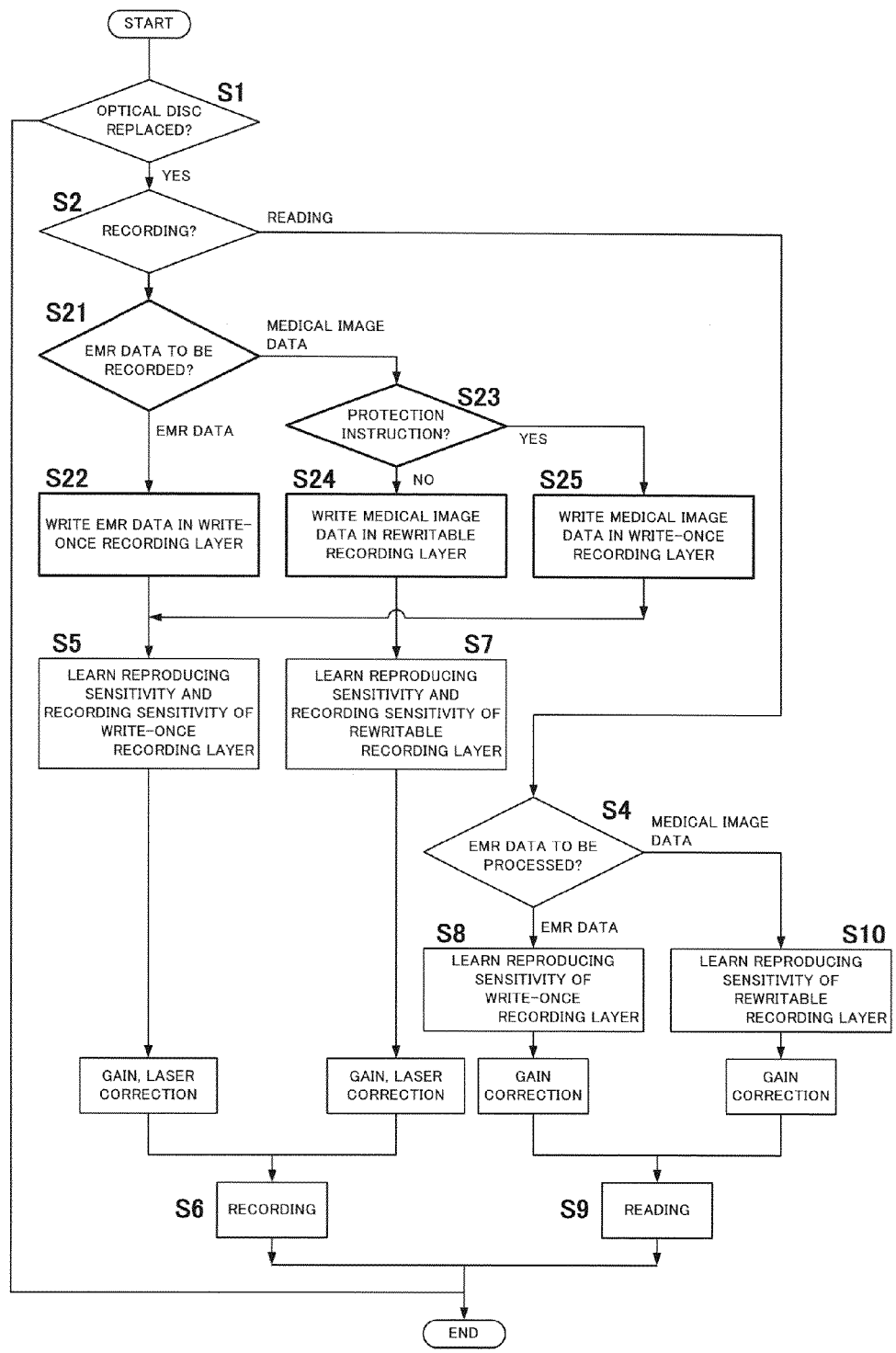
FIG. 12 is a flowchart showing a processing flow of the principal part of a medical-data access control unit in a data management device according to a second embodiment of the present invention.

FIG. 12 is a flowchart showing a processing flow of the principle part of a medical-data access control unit 33 in a medical-data management device 1 according to a second embodiment of the present invention.

In the first embodiment, medical data to be recorded is received by the medical-data management device and is automatically determined by the medical data determination unit 32. EMR data is written in the write-once recording layer 18 of the optical disc 14 while medical image data is written in the rewritable recording layers 16 and 17. However, medical image data used for determining, for example, the name of a patient's disease (definite diagnosis) by a doctor needs to be recorded in the write-once recording layer 18 instead of the rewritable recording layers 16 and 17 of the optical disc 14 to prevent overwriting. In the medical-data management device of the second embodiment, the medical-data access control unit 33 is operated as shown in FIG. 12.

In step S21, it is determined whether the determination result of a medical data determination unit 32 is EMR data or medical image data. In the case where it is determined in step S21 that EMR data is to be processed, step S22 is performed to write the EMR data to be processed in a write-once recording layer 18 of an optical disc 14.

In the case where it is determined in step S21 that medical image data is to be processed, step S23 is performed. In the case where medical image data used for a definite diagnosis is to be processed, a radiologist prepares a definite diagnosis report from a client terminal 6*a*. A definite diagnosis flag is displayed on the report. The data to be processed is then stored in a picture archiving and communication system server 5 so as not to be rewritten by the flag. When the data to be processed is outputted from the picture archiving and communication system server 5 to the medical-data management device 1, a protection instruction is additionally outputted.

A protection instruction 55 is demodulated by an IF circuit 10 through a hospital LAN 2 and then is outputted to the medical-data access control unit 33 as indicated by a broken line in FIG. 4. In step S23, the medical-data access control unit 33 determines the presence or absence of the protection instruction 55.

In the case where the protection instruction 55 is not detected in step S23, an optical pickup 27 accesses proper one of rewritable recording layers 16 and 17 in step S24 to write medical image data to be processed into the rewritable recording layer.

In the case where the protection instruction 55 is detected in step S23, medical image data to be processed is not overwritten even though it is medical image data. Step S25 is performed to cause the optical pickup 27 to access the write-once recording layer 18 to write the medical image data to be processed in the write-once recording layer 18 in a protected manner.

Third Embodiment

Figure 13:
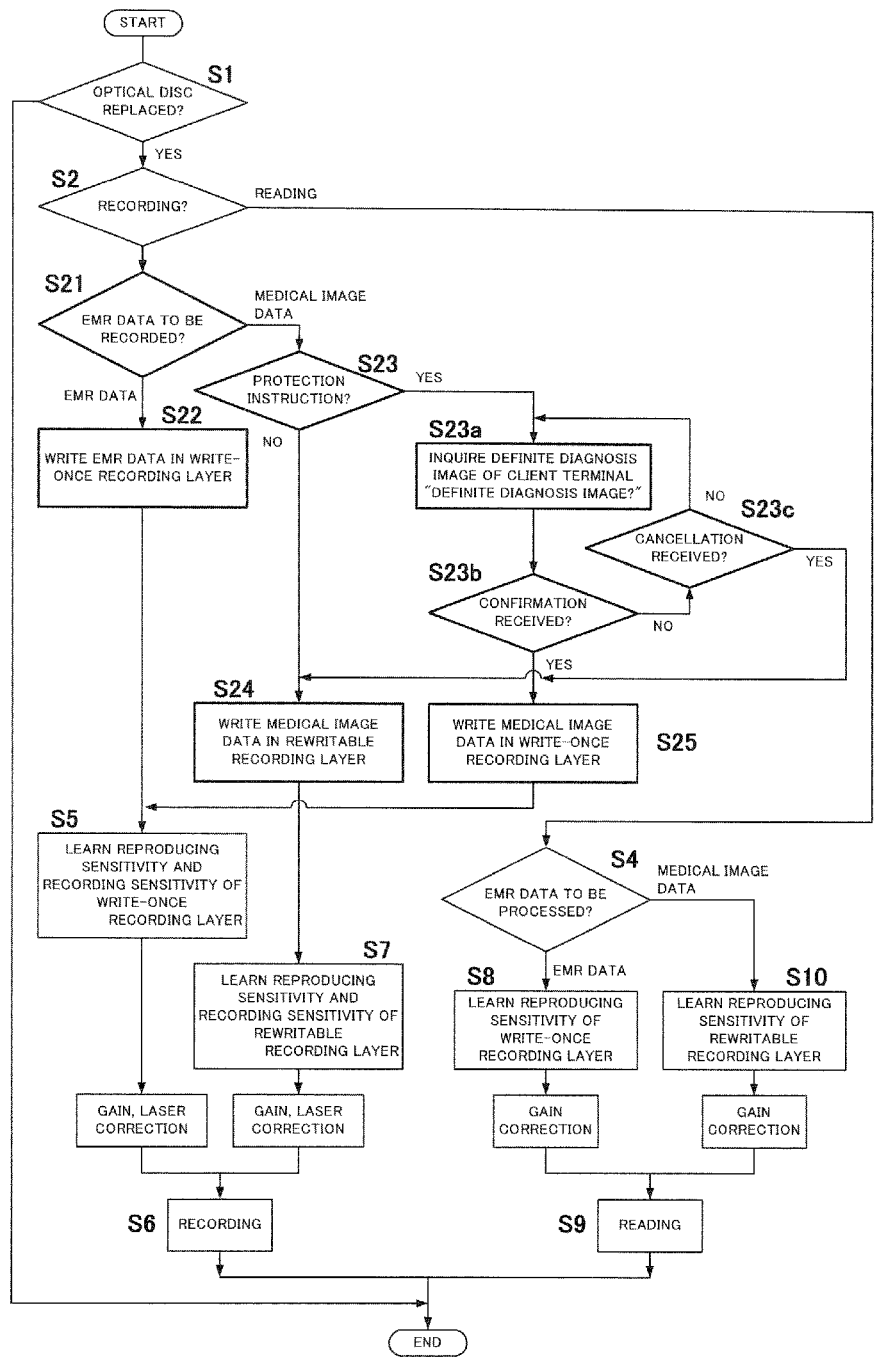
FIG. 13 is a flowchart showing a processing flow of the principal part of a medical-data access control unit in a data management device according to a third embodiment of the present invention.

FIG. 13 is a flowchart of the principal part of a medical-data access control unit 33 in a medical-data management device 1 according to a third embodiment of the present invention.

In the second embodiment, in the case where the protection instruction 55 is detected in step S23, step S25 is immediately performed to write medical image data to be processed in the write-once recording layer 18 in a protected manner. In the third embodiment, an inquiry is automatically transmitted sequentially to client terminals 6*a* to 6*c* from the medical-data management device 1 through a hospital LAN 2.

Specifically, a subroutine including steps S23*a*, S23*b*, and step S23*c* is added between step S23 and step S25. Other steps are identical to those of the second embodiment.

In step S23*a*, an inquiry about whether an image is "definite diagnosis image" or not is transmitted to the client terminals 6*a* to 6*c*. As indicated by a broken line in FIG. 4, an inquiry signal 56 is transmitted to the client terminals 6*a* to 6*c* from the medical-data access control unit 33 and an IF circuit 10 through the hospital LAN 2. The screens of the client terminals 6*a* to 6*c* having received the inquiry signal 56 display, for example, a sentence "Confirm the received instruction." and an instruction "Press the return key to confirm the instruction. Press the function key F12 to cancel the instruction."

In step S23*b* following step S23*a*, whether the return key has been operated or not on the client terminals 6*a* to 6*c* is checked. In the case where an operation of the return key is not detected in step S23*b*, whether the function key F12 has been operated or not on the client terminals 6*a* to 6*c* is checked in step S23*c*. In the case where an operation on the function key F12 is not detected in step S23*c*, the process returns to step S23*a*.

Thus, in the case where the return key is operated on the client terminals 6*a* to 6*c*, the medical-data access control unit 33 detects the operation in step S23*b* and recognizes that "confirmation" has been received again, so that step S25 is performed. In the case where the function key F12 is operated instead of the return key on the client terminals 6*a* to 6*c*, the medical-data access control unit 33 detects the operation in step S23*c* and recognizes that "cancellation of confirmation" has been received, so that step S24 is performed.

The provision of the subroutine of steps S23*a* to S23*c* can prevent medical image data used for a definite diagnosis from being erroneously written in a write-once recording layer 18, thereby avoiding a reduction in the reliability of an EMR.

Fourth Embodiment

As illustrated in FIG. 1, the two servers are provided in the first embodiment. One of the servers is the picture archiving and communication system server 5 and the other is the electronic medical record (EMR) system 7.

Figure 14:
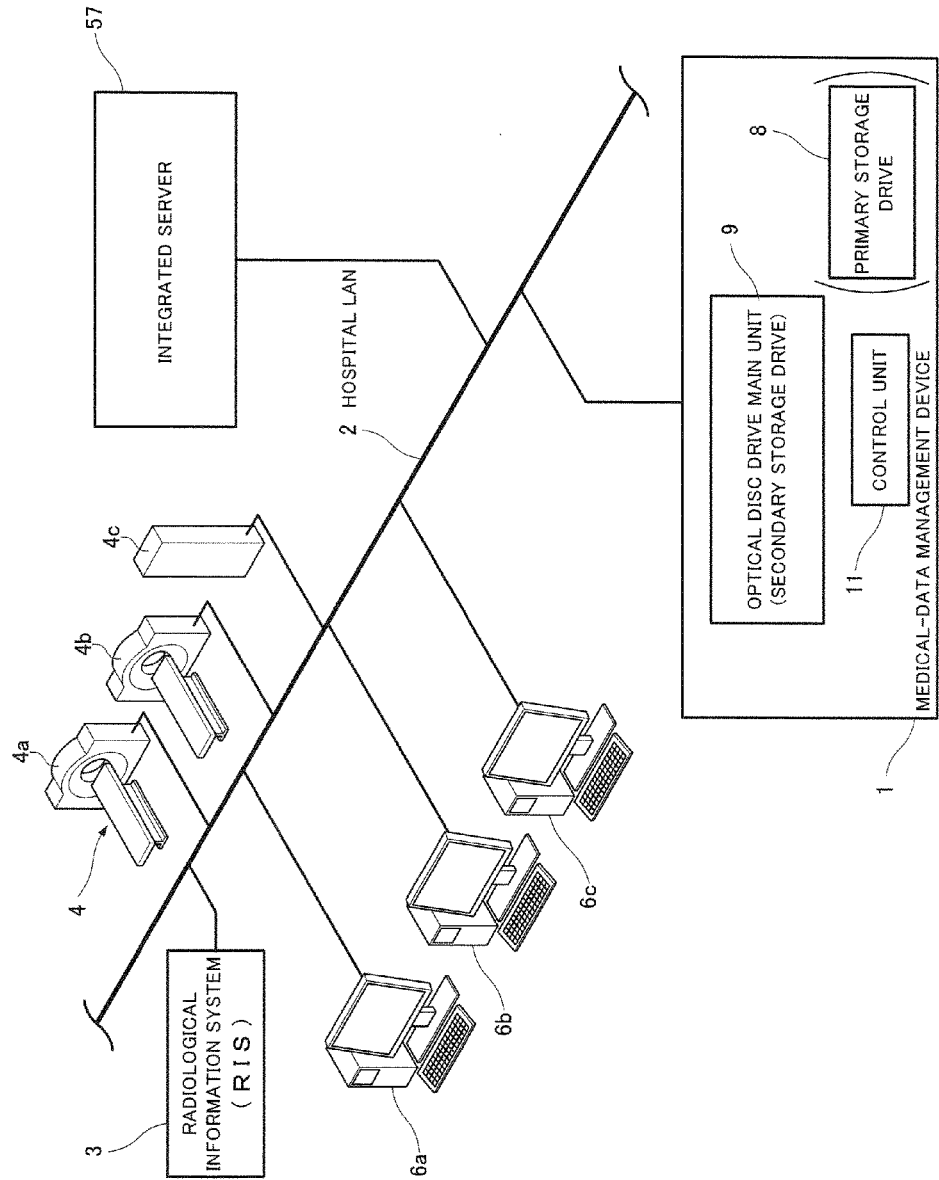
FIG. 14 is a system diagram of a hospital using a data management device according to a fourth embodiment of the present invention.

As illustrated in FIG. 14 of the present embodiment, a system may be configured with an integrated server 57 that is a combination of the two servers. As illustrated in FIG. 14, a medical-data management device 1, a client terminal 6*a*, and the integrated server 57 are connected via a hospital LAN 2 as in the first embodiment.

Figure 15:
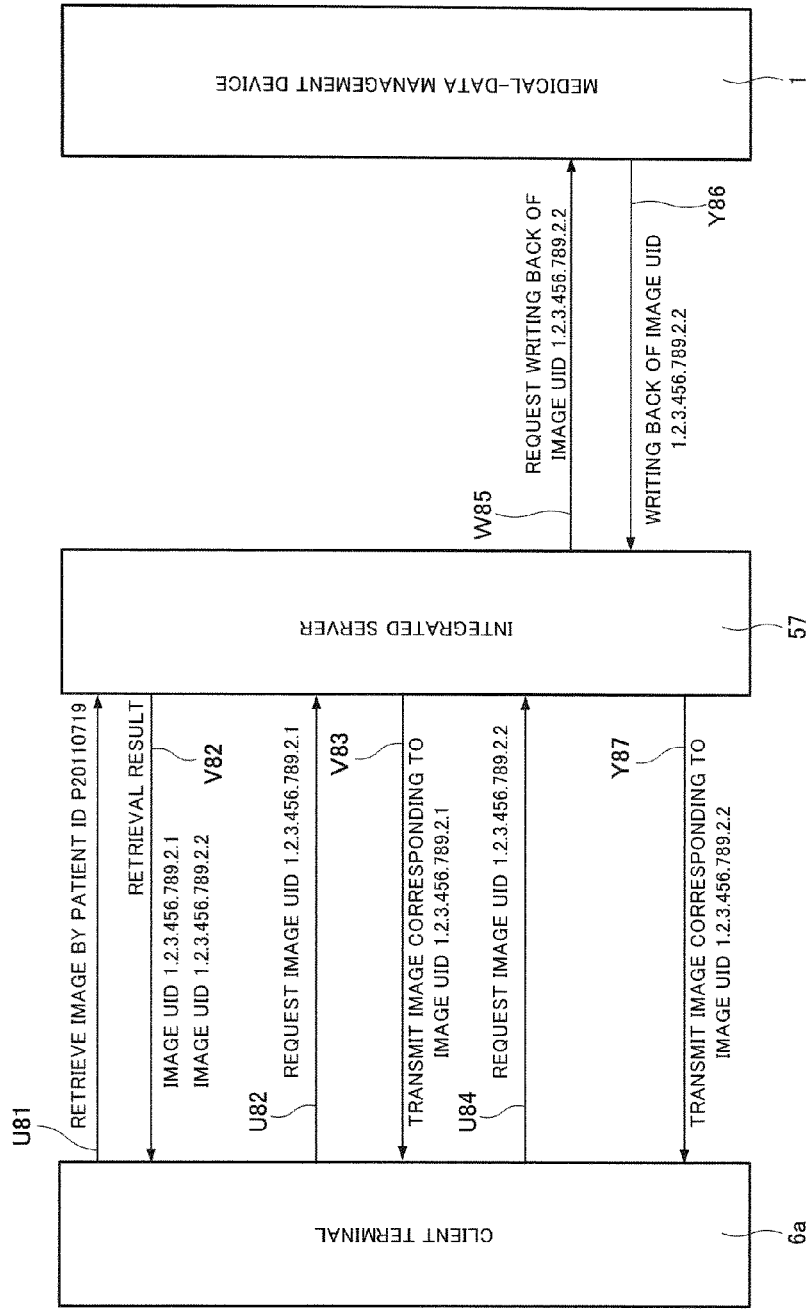
FIG. 15 is a schematic diagram of communications for explaining the fourth embodiment of the present invention.

FIG. 15 is a block diagram of a communication procedure for processing in which EMR data and medical image data that are temporarily duplicated and stored on an optical disc 14 of the medical-data management device 1 are managed by the single integrated server 57 connected to the hospital LAN 2, and the EMR data is viewed and caused to contain additional data on the given client terminal 6*a*, and processing in which medical image data is viewed, added, and rewritten.

For example, data is monthly or yearly stored on the optical disc 14. When the hard disk of the integrated server 57 is filled with data, a file not accessed from the terminal may be erased because its original file remains on the optical disc 14.

In order to view a data file of the optical disc 14 again by accessing the file under such circumstances, the file is accessed by a doctor, a radiologist, or a nurse from the client terminal 6*a* as in the following example:

When a doctor accesses the integrated server 57 from the client terminal 6*a* to refer to patient's medical image data captured and stored in the past, in many cases, a QR command (Query/Retrieve command) of the DICOM standard is transmitted or received.

DICOM communications (or corresponding communications between devices) are carried out between the client terminal 6*a* and the integrated server 57 via a communication sequence U81 in FIG. 15. Specifically, a patient ID "P20110719" is transmitted from the client terminal 6*a* to the integrated server 57 to instruct the integrated server 57 to retrieve an image.

The integrated server 57 having detected the ID returns an image matching the patient ID "P20110719" stored in an HDD disk in the server, and a list of UIDs (unique IDs) that specify the image, to the terminal as a retrieval result via a communication sequence V82.

The doctor then requests a specific image "1.2.3.456.789.2.1" in the displayed list via a communication sequence U82. The integrated server having received the request transmits corresponding image data to the terminal 6a via a communication sequence V83 when the HDD in the server contains an image data body.

When the doctor acting as an operator requests another image UID "1.2.3.456.789.2.2" via a communication sequence U84, in the case where corresponding image data is not found in the HDD of the integrated server, the image data is moved to the medical-data management device and is erased from the server. Thus, the integrated server issues a writing-back request command W85 to the medical-data management device. The medical-data management device having received the command detects the occurrence of the QR command beforehand through an IF circuit 10 by means of a medical data determination unit 32 included in a system controller 26, and thus the medical-data management device recognizes that access to medical image data is requested from the integrated server 57.

In the case where the medical data determination unit 32 determines access to medical image data, the optical disc 14 is operated by rotation. Since EMR data stored in a write-once recording layer 18 is not necessary, a layer access control unit 34 drives an objective lens 36 and a spherical aberration correction lens 41 to focus and track a rewritable recording layer 16 or a rewritable recording layer 17, moves to the layer containing desired medical data, reads a medical image data body corresponding to 1.2.3.456.789.2.2, transmits the image body to the integrated server 57 via a writing-back response Y86 through the IF circuit 10, and transmits corresponding image data to the terminal via a communication sequence Y87 after the data is written back.

In the case of access to the EMR data from the client terminal 6a, DICOM communications (or corresponding communications between devices) are not carried out between the client terminal 6a and the medical-data management device 1. In this case, the medical data determination unit 32 included in the system controller 26 determines a request of access to EMR data from the integrated server 57 because communications between devices are not carried out through the IF circuit 10.

In the case where access to EMR data is determined, the optical disc 14 is started by rotation. Since medical image information stored in the rewritable recording layer is not necessary, the objective lens 36 and the aberration correction lens 37 are driven to focus and track the write-once recording layer 18, move to the layer containing desired EMR data to read the data, and temporarily write back the data into the integrated server 57 through the IF circuit 10. The integrated server 57 then transmits a file to a client terminal 6c after the file is written back.

Communications between devices may be performed or not before reading of data, depending upon the type of data requested by each of the client terminals. Thus, a servo is drawn to the rewritable recording layers 16 and 17 containing directly requested data or the write-once recording layer 18, and an operation is started and completed only in the layer, allowing recording/learning or servo learning in all the layers so as to shorten the startup of the optical disc 14 from several tens seconds.

Access may be almost simultaneously made from the client terminals 6a to 6c. In this case, the optical disc 14 is fully operated to perform learning on all the layers.

However, an access request to an EMR or medical image data from, for example, the client terminal 6a of an examination room may be given a higher priority, and then the write-once recording layer 18 or the rewritable recording layers 16 and 17 may be determined as an operated layer according to the data.

The provision of a DICOM communication function or a hard disk drive as a primary storage area in the medical-data management device 1 makes it possible to directly transmit a command from the client terminals 6a to 6c without passing through the integrated server 57, thereby more quickly capturing a medical image stored on the optical disc and referring to the image.

Fifth Embodiment

Figure 16:
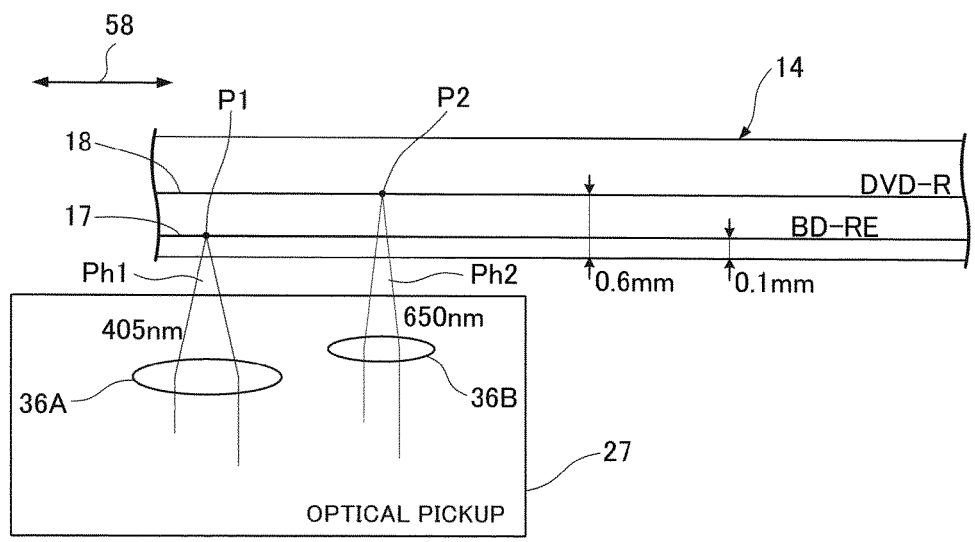
FIG. 16 is a conceptual diagram of a multi-disc in which a BD-RE recording film is used as a rewritable recording layer and a DVD-R recording film is used as a write-once recording layer in an optical disc of a data management device according to a fifth embodiment of the present invention.
Figure 17:
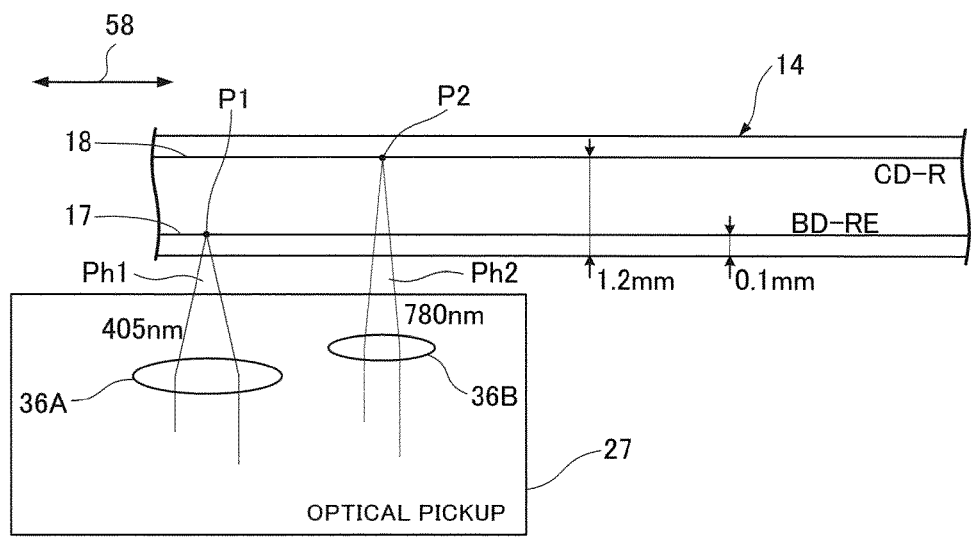
FIG. 17 is a conceptual diagram of a multi-disc in which a BD-RE recording film is used as the rewritable recording layer and a CD-R recording film is used as the write-once recording layer in the optical disc of the data management device according to the fifth embodiment of the present invention.
Figure 18:
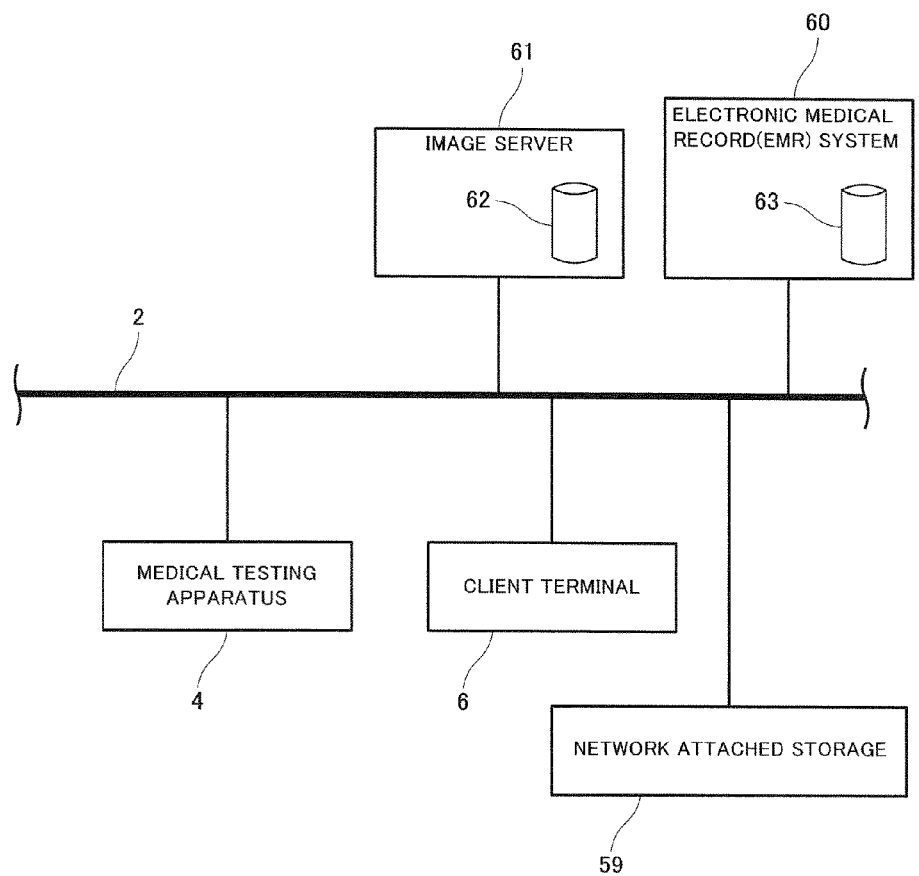
FIG. 18 is a connection diagram of a conventional hospital LAN.

FIGS. 16 and 17 are conceptual diagrams illustrating a fifth embodiment according to the present invention.

FIG. 16 is a conceptual diagram of a multi-disc in which a rewritable recording layer 17 of an optical disc 14 is a recording film used for a BD-RE (Blu-ray Disc Rewritable) while a write-once recording layer 18 is a recording film used for a DVD-R (DVD Recordable Disc). FIG. 17 is a conceptual diagram of a multi-disc in which the rewritable recording layer 17 of the optical disc 14 is a recording film used for a BD-RE (Blu-ray Disc Rewritable) while the write-once recording layer 18 is a recording film used for a CD-R (CD Recordable Disc).

In the foregoing embodiments, the light source 38 of the optical pickup 27 has a single wavelength, and the aberration correction lens 37 is moved by the driving device 51 depending upon the accessed recording layer to focus the laser beam Ph onto the desired recording layer as illustrated in FIGS. 6(a) and 6(b). In the event of an external impact, the objective lens 36 is shifted so as to cause defocusing from the desired recording layer onto another layer. Recorded data in the layer may be damaged during recording.

In the fifth embodiment, a light source 38 of an optical pickup 27 is a semiconductor laser element that can emit a laser beam Ph with a switched wavelength. Such a dual-wavelength semiconductor laser element is generally known as an element for a multi-drive that accesses a CD (Digital Versatile Disc) and a DVD (Digital Versatile Disc) by means of a single optical pickup device. As illustrated in FIG. 16, in the case of a multi-disc in which the rewritable recording layer 17 of the optical disc 14 is a recording film used for BD-RE (Blu-ray Disc Rewritable) while the write-once recording layer 18 is a recording film used for DVD-R (DVD Recordable Disc), the optical pickup 27 includes a first objective lens 36A that causes a laser beam Ph1 having a wavelength of 405 nm to access the rewritable recording layer 17, and a second objective lens 36B that causes a laser beam Ph2 having a wavelength of 650 nm to access the write-once recording layer 18. A distance between a focal position P1 of the laser beam Ph1 and a focal position P2 of the laser beam Ph2 is preset as a distance between the write-once recording layer 18 and the rewritable recording layer 17 of the used optical disc 14. Reference numeral 58 denotes the radial direction of the optical disc 14.

The optical pickup 27 controlled by a servo control circuit 25 switches the dual-wavelength semiconductor laser element of the light source 38 to emit light with a wavelength of 405 nm in the case of reading and writing of medical image data, thereby irradiating the rewritable recording layer 17 with the laser beam Ph1 so as to enable reading and writing. In the case of reading and writing of EMR data, the dual-wavelength semiconductor laser element of the light source 38 is switched so as to emit light with a wavelength of 650 nm, thereby irradiating the write-once recording layer 18 with the laser beam Ph2 so as to enable reading and writing.

In the case of the optical pickup 27 on which the distance between the focal position P1 of the laser beam Ph1 and the focal position P2 of the laser beam Ph2 is preset as the distance between the rewritable recording layer 17 and the write-once recording layer 18, when access is switched between the rewritable recording layer 17 and the write-once recording layer 18, the aberration correction lens 37 does not need to be mechanically moved by the driving device 51 unlike in FIG. 6. Furthermore, a BD laser beam (405 nm) cannot access the write-once recording layer 18, whereas a DVD laser beam (650 nm) cannot access the rewritable recording layer 17. Thus, even the application of an impact does not move the laser beam between the layers with constant recording power, thereby improving impact resistance.

As illustrated in FIG. 17, in the case of a multi-disc in which the rewritable recording layer 17 is a recording film used for BD-RE while the write-once recording layer 18 is a recording film used for CD-R, the optical pickup 27 includes a dual-wavelength semiconductor laser element that switches and outputs the laser beam Ph1 having a wavelength of 405 nm and the laser beam Ph2 having a wavelength of 780 nm.

In FIGS. 16 and 17, the first objective lens 36A and the second objective lens 36B are arranged in the radial direction of the optical disc 14. The first objective lens 36A and the second objective lens 36B may be arranged in the circumferential direction of the optical disc 14.

EMR data has a smaller volume than medical image data. In this respect, the present embodiment is suitable for a clinic admitting a smaller number of patients.

INDUSTRIAL APPLICABILITY

The medical-data management device of the present invention can contribute to improvement of the reliability and operability of medical data management used for medical administration, medical education, clinical training data, and so on.

REFERENCE SIGNS LIST 1 medical-data management device
2 hospital LAN
3 radiological information system
4 medical testing apparatus
4a, 4b MRI apparatus
4c X-ray apparatus
5 picture archiving and communication system server
6a to 6c client terminal
7 electronic medical record (EMR) system
8 primary storage drive
9 optical disc drive main unit
10 interface circuit
11 control unit
12 optical disc with cartridge
13 cartridge
14 optical disc
15 shutter
16, 17 rewritable recording layer
18 write-once recording layer
Ph laser beam
22 disc motor
24 motor driving circuit
25 servo control circuit
26 system controller
27 optical pickup
28 laser driving circuit
32 medical data determination unit
33 medical-data access control unit
34 layer access control unit
35 layer learning unit
36 objective lens
37 aberration correction lens
51 driving device
55 protection instruction
56 inquiry signal
57 integrated server
36A first objective lens
36B second objective lens

The invention claimed is:

1. A medical-data management device that records medical data on an optical disc including a rewritable recording layer and a write-once recording layer,
the medical-data management device comprising:
a medical data determination unit that determines whether the medical data to be recorded on the optical disc is electronic medical record (EMR) data or not; and
a medical-data access control unit that causes an optical pickup to access the write-once recording layer of the optical disc to write the data in a case where the medical data to be recorded according to a determination result of the medical data determination unit is EMR data, and causes the optical pickup to access the rewritable recording layer of the optical disc to write the data in a case where the medical data is not EMR data, wherein
in the case where the medical data to be recorded according to a determination result of the medical data determination unit is EMR data, the medical-data access control unit writes the data while irradiating, from the optical pickup, the write-once recording layer of the optical disc with a laser beam having a first wavelength suitable for recording on the write-once recording layer, and
in the case where the medical data is not EMR data, the medical-data access control unit writes the data while irradiating, from the optical pickup, the rewritable recording layer of the optical disc with a laser beam having a second wavelength suitable for recording on the rewritable recording layer.

2. The medical-data management device according to claim 1, wherein the medical data determination unit determines whether the medical data is EMR data or not by identifying one of a flag and a tag at a beginning of the medical data to be recorded, or determining presence or absence of a specific code in predetermined bytes from the beginning of the medical data.

3. The medical-data management device according to claim 1, wherein in the case where the medical data to be recorded according to a determination result of the medical data determination unit is EMR data, the medical-data access control unit writes the data after relocating an optical element in an optical path so as to focus a laser beam onto the write-once recording layer of the optical disc from the optical pickup, and
in the case where the medical data is not EMR data, the medical data access control unit writes the data after relocating the optical element in the optical path so as to focus the laser beam onto the rewritable recording layer of the optical disc.

4. The medical-data management device according to claim 1, further comprising a layer learning unit that learns recording sensitivity of the optical disc when medical data is recorded on the optical disc,
wherein in the case where the medical data to be recorded according to a determination result of the medical data determination unit is EMR data, the layer learning unit learns recording sensitivity of the write-once recording layer out of the write-once recording layer and the rewritable recording layer of the optical disc, and in the case where the medical data to be recorded according to a determination result of the medical data determination unit is not EMR data, the layer learning unit learns recording sensitivity of the rewritable recording layer out of the write-once recording layer and the rewritable recording layer of the optical disc.

5. The medical-data management device according to claim 1, wherein in the case where the medical data to be recorded according to a determination result of the medical data determination unit is not EMR data and a protection instruction is detected, the medical-data access control unit causes the optical pickup to access the write-once recording layer of the optical disc to write the data.

6. The medical-data management device according to claim 1, wherein in the case where the medical data to be recorded according to a determination result of the medical data determination unit is not EMR data and a confirmation instruction inputted from a client server terminal is detected, the medical-data access control unit makes an inquiry to the client server terminal, and then only in a case where reception of a protection instruction from the client server terminal is detected, the medical-data access control unit causes the optical pickup to access the write-once recording layer of the optical disc to write the data.

7. The medical-data management device according to claim 1, wherein the medical data is one of EMR data containing information specifying a patient and test result information outputted from a medical testing apparatus having tested a specified part of the patient.

8. The medical-data management device according to claim 7, wherein the test result information is data complying with a format of medical images captured by the medical testing apparatus and a DICOM (Digital Imaging and Communication in Medicine) standard that defines a communication protocol between medical imaging apparatuses for these images.

9. A medical-data management device that reads medical data from an optical disc including a rewritable recording layer and a write-once recording layer, the medical-data management device comprising:
a medical data determination unit that determines whether the medical data to be read from the optical disc is EMR data or not; and
a medical-data access control unit that causes an optical pickup to access the write-once recording layer of the optical disc to read the data in a case where the medical data to be read according to a determination result of the medical data determination unit is EMR data, and causes the optical pickup to access the rewritable recording layer of the optical disc to read the data in a case where the medical data is not EMR data, wherein in the case where the medical data to be recorded according to a determination result of the medical data determination unit is EMR data, the medical-data access control unit reads the data while irradiating, from the optical pickup, the write-once recording layer of the optical disc with a laser beam of the optical pickup having a first wavelength, and in the case where the medical data is not EMR data, the medical-data access control unit reads the data while irradiating, from the optical pickup, the rewritable recording layer of the optical disc with a laser beam of the optical pickup having a second wavelength.

10. The medical-data management device according to claim 9, wherein the medical data determination unit determines that the medical data is not EMR data by determining whether or not a data requesting command complies with a DICOM standard.

11. The medical-data management device according to claim 9, wherein the medical data determination unit determines that the medical data is not EMR data by determining whether or not requested data is image data complying with a DICOM standard.

12. The medical-data management device according to claim 9, wherein in the case where the medical data to be read according to a determination result of the medical data determination unit is EMR data, the medical-data access control unit reads the data after relocating an optical element in an optical path so as to focus a laser beam of the optical pickup onto the write-once recording layer of the optical disc, and in the case where the medical data is not EMR data, the medical-data access control unit reads the data after relocating the optical element in the optical path so as to focus the laser beam onto the rewritable recording layer of the optical disc.

13. The medical-data management device according to claim 9, further comprising a layer learning unit that learns one of recording sensitivity and reproducing sensitivity of the optical disc when medical data is reproduced from the optical disc, wherein in the case where the medical data to be read according to a determination result of the medical data determination unit is EMR data, the layer learning unit learns reproducing sensitivity of the write-once recording layer out of the write-once recording layer and the rewritable recording layer of the optical disc, and in the case where the medical data to be read according to a determination result of the medical data determination unit is not EMR data, the layer learning unit learns reproducing sensitivity of the rewritable recording layer out of the write-once recording layer and the rewritable recording layer of the optical disc.

14. The medical-data management device according to claim 9, wherein the medical data is one of EMR data containing information specifying a patient and test result information outputted from a medical testing apparatus having tested a specified part of the patient.

15. The medical-data management device according to claim 14, wherein the test result information is data complying with a format of medical images captured by the medical testing apparatus and a DICOM standard that defines a communication protocol between medical imaging apparatuses for these images.

* * * * *